(12) United States Patent
Truong

(10) Patent No.: US 8,304,454 B2
(45) Date of Patent: Nov. 6, 2012

(54) ANTIMICROBIAL CELLULOSE SPONGE AND METHOD OF MAKING

(75) Inventor: Myhanh T. Truong, Cottage Grove, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 206 days.

(21) Appl. No.: 12/329,947

(22) Filed: Dec. 8, 2008

(65) Prior Publication Data

US 2009/0163598 A1   Jun. 25, 2009

Related U.S. Application Data

(60) Provisional application No. 61/015,794, filed on Dec. 21, 2007.

(51) Int. Cl.
*A61K 31/155* (2006.01)
(52) U.S. Cl. ....................................................... 514/635
(58) Field of Classification Search .................. None
See application file for complete search history.

(56) References Cited

U.S. PATENT DOCUMENTS

| | | | |
|---|---|---|---|
| 2,609,270 A | 9/1952 | Couper | |
| 2,945,772 A | 7/1960 | James et al. | |
| 3,018,192 A | 1/1962 | Hennemann et al. | |
| 3,055,765 A | 9/1962 | Petrucci | |
| 3,197,327 A | 7/1965 | Dillon | |
| 3,954,493 A | 5/1976 | Battista et al. | |
| 4,675,347 A | 6/1987 | Mochizuki et al. | |
| 4,678,704 A | 7/1987 | Fellows | |
| 4,940,631 A | 7/1990 | Colin et al. | |
| 5,441,742 A | 8/1995 | Autant et al. | |
| 5,541,233 A | 7/1996 | Roenigk | |
| 5,700,742 A | 12/1997 | Payne | |
| 5,700,754 A | 12/1997 | Inui et al. | |
| 5,993,840 A | 11/1999 | Fawkes et al. | |
| 6,017,561 A * | 1/2000 | Zhou et al. | 424/486 |
| 6,235,302 B1 | 5/2001 | Mans et al. | |
| 6,270,754 B1 | 8/2001 | Zhou et al. | |
| 6,375,967 B1 | 4/2002 | Bedue et al. | |
| 6,706,855 B1 | 3/2004 | Collins et al. | |
| 6,841,527 B2 * | 1/2005 | Mitra et al. | 510/295 |
| 6,951,834 B2 | 10/2005 | Mitra et al. | |
| 7,094,741 B2 | 8/2006 | Barnabas et al. | |
| 2003/0099570 A1 * | 5/2003 | Barnabas et al. | 422/28 |
| 2007/0048344 A1 | 3/2007 | Yahiaoui et al. | |
| 2007/0048356 A1 | 3/2007 | Schorr et al. | |
| 2007/0048358 A1 | 3/2007 | Schorr et al. | |

FOREIGN PATENT DOCUMENTS

| | | |
|---|---|---|
| EP | 0 358 572 A1 | 3/1990 |
| EP | 1473047 B1 | 10/2006 |
| GB | 2300200 A | 10/1996 |
| GB | 2408516 A | 6/2005 |
| WO | WO 9844791 A1 | 10/1998 |
| WO | WO 0203899 A1 | 1/2002 |

OTHER PUBLICATIONS

Reitsma et al., "Effectiveness of a New Antimicrobial Gauze Dressing as a Bacterial Barrier", Sep. 2001.

* cited by examiner

*Primary Examiner* — Susan Tran
*Assistant Examiner* — Jessica Worsham
(74) *Attorney, Agent, or Firm* — Trisha D. Adamson

(57) ABSTRACT

Biguanide bonded within a cellulose sponge inhibits or prevents the growth of microorganisms such as bacteria, mold, and fungus within the cellulose sponge over the useful life of the cellulose sponge.

13 Claims, No Drawings

ANTIMICROBIAL CELLULOSE SPONGE AND METHOD OF MAKING

CROSS-REFERENCE TO RELATED APPLICATION

This application claims priority to U.S. Provisional Patent Application No. 61/015,794, filed Dec. 21, 2007, the disclosure of which is incorporated by reference herein in its entirety.

FIELD

The present disclosure relates to cellulose sponges and a method of making a cellulose sponge permanently antimicrobial throughout the useful life of the cellulose sponge.

BACKGROUND

Cellulose sponges can be used for cleaning a variety of surfaces. They are generally packaged for sale to consumers in a slightly moist condition to keep them soft, and include an antimicrobial agent to prevent microorganism growth during storage shelf-life. However, cellulose sponges are notoriously prone to bacterial and mold growth during use because of a chronically moist environment. Often, the antimicrobial agent present during storage is rinsed out or becomes inactive or insufficient during the life of the cellulose sponge. Therefore, the microorganisms growing in the sponge can present a health concern in the home since cellulose sponges are commonly used in kitchens and bathrooms. There is a tremendous need for a cellulose sponge that has greater resistance to microorganism growth during use.

SUMMARY

While antimicrobial agents normally used to preserve cellulose sponges in their packaging do not continue working during subsequent use, it has now been found that a particular antimicrobial agent known as biguanide used in sufficient concentration provides remarkable, lasting results. Biguanide remains bonded within the cellulose sponge despite repeated washings. When at least 0.02% wt. biguanide, by dry sponge weight, remains present and active throughout the useful life of the sponge, there remains a dramatic reduction in microbial growth within the cellulose sponge.

For example, even following 100 cycles of rinsing and wringing with water, a cellulose sponge treated with biguanide to maintain at least 0.02% wt. biguanide shows a three log reduction in microorganism growth. This is a major breakthrough and, although biguanide was known as an antimicrobial agent for conventional uses, this unique use of biguanide to create an essentially permanently antimicrobial cellulose sponge has potentially important public health benefits.

It is hypothesized that, unlike many other antimicrobial agents, the cationic functionality of biguanide bonds with anionic functionality of cellulose sponge material thereby not only retaining the biguanide in place, but doing so in a way the allows the biguanide to remain active and able to reduce in microbial within short period of time.

The present invention thus provides cellulose sponge with an antimicrobial agent retained within the cellulose sponge that inhibits or prevents the growth of microorganisms such as bacteria, mold, and fungus within the cellulose sponge over the useful life of the cellulose sponge. In one embodiment, the cellulose sponge with the antimicrobial is packaged in a sealed container, possibly containing moisture. In such a package, it may be desirable to also include a humectant in the antimicrobial cleaning article to lower the water activity within the package and prevent growth of microorganism within the package.

In one embodiment, the cellulose sponge comprises biguanide. The cellulose sponge maintains at least 0.02% wt. biguanide, based on the dry weight of the cellulose sponge, following 100 cycles of rinsing and wringing with water to provide at least a three log reduction in microorganisms in the cellulose sponge.

In another embodiment the cellulose sponge in a package comprises at least 0.4% wt. biguanide, based on the dry weight of the cellulose sponge. Following removal from the package and 100 cycles of rinsing and wringing with water at least 0.02% wt. biguanide, based on the dry weight of the cellulose sponge, remains in the sponge to provide at least a three log reduction in microorganisms in the cellulose sponge.

In another embodiment, the cellulose sponge is made by a process comprising providing a cellulose sponge, absorbing into the cellulose sponge an input solution comprising 0.1 to 2.0% wt. biguanide, and packaging the cellulose sponge in a sealed package. The packaged cellulose sponge comprises at least 0.4% wt. biguanide, based on a dry weight of the cellulose sponge.

In another embodiment, the cellulose sponge in a package comprises at least 1.25% wt. biguanide based on the dry weight of the cellulose sponge and a humectant resulting in a water activity ($a_w$) in the package of less than 0.91. Following removal of the cellulose sponge from the package and 100 cycles of rinsing and wringing with water with water at least 0.5% wt. biguanide, based on the dry weight of the cellulose sponge, remains in the cellulose sponge to provide a 100% reduction of microorganisms in the sponge.

In another embodiment, the method of making an antimicrobial cleaning article comprises providing a cellulose sponge, absorbing into the cellulose sponge a input solution containing at least 0.1% wt. biguanide, bonding the biguanide within the cellulose sponge, packaging the cellulose sponge in a sealed package, wherein the packaged cellulose sponge contains at least 0.4% wt. biguanide, based on a dry weight of the cellulose sponge.

In another embodiment, the method of maintaining the ability of a cleaning structure to be antimicrobial comprises providing a cellulose sponge comprising anionic functional groups, absorbing into the cellulose sponge an input solution comprising biguanide having cationic functional groups, bonding the cationic functional groups of the biguanide to the anionic functional groups of the cellulose sponge, repeatedly exposing the cellulose sponge to water for rinsing. The bonded biguanide provides at least a three log reduction in the number of microorganisms within the cellulose sponge.

It will also be understood that other antimicrobial agents having a cationic functional group providing sufficient bonding to achieve long-term active residence to microbial growth within the cellulose sponge material will be useful according to the present disclosure.

DETAILED DESCRIPTION

For a cleaning article to be usable over a period of time, the cleaning article itself should not be a source of housing and spreading microorganisms during the cleaning process. As long as the proper environment for the growth of microorganisms exists, the cleaning article can degrade. Bacteria and fungi are the microorganisms that are generally responsible for degrading products, particularly when degradation occurs in the package prior to use. Bacteria require a carbon source, proper atmosphere, the proper environmental temperature and pH, and moisture to grow. Fungi have similar growth requirements, except that all fungi need oxygen, and the needed moisture levels vary over a wider range than for bacteria. Growth is defined here as the increase in the total bacterial population, rather than the enlargement of individual bacterial cells.

Sponges are a common cleaning article. Sponges are light, fibrous connective structures which have absorbent qualities. They can be made from a variety of different materials including synthetic polymers such as urethanes and naturally polymeric cellulose, referred to herein as cellulose sponge. Cellulose sponge is a unique cleaning article because of its excellent water adsorption qualities. Cellulose sponge is highly hydrophilic with a water-holding capacity 10 times its own weight. Cellulose sponge also demonstrates excellent wet strength and is capable of both donating fluid and absorbing liquid.

Generally, a cellulose sponge is made by dispersing sodium sulfate crystals in viscose cellulose. Once mixed with the viscose cellulose, the sodium sulfate crystals are melted out of the cellulose sponge by heating the viscose cellulose while the viscose cellulose is regenerated or coagulated to an insoluble state. This creates the pores in the cellulose sponge, which contributes to its high water adsorption. Once regenerated, the viscose cellulose sponge is rinsed. It is understood that the cellulose sponge may be made from a variety of cellulose containing raw materials such as, but not limited to, wood, wood pulp, recycled cellulose sponges, or other natural fibers. It is understood that the cellulose sponge may contain additional materials such as dyes, perfumes, fragrances, surfactants, and reinforcing fibers. Reinforcing fibers may be natural fibers, tissue dust, open shredded pulp fiber, cotton fibers. Natural fibers include cotton, wool, silk, hemp, bamboo, viscose fibers such as rayon.

The excellent water adsorption qualities of cellulose sponge can create drawbacks. The moisture adsorbed into the cellulose sponge can contain unwanted microorganisms. Once adsorbed into the cellulose sponge, the microorganisms may remain, thrive, and multiply in the moist environment found within the cellulose sponge. The microorganisms may raise health and safety concerns. For example, during cleaning, various microorganisms within the cellulose sponge may be transferred to other surfaces that the users believe they are cleaning, when in fact they are spreading microorganisms over other surfaces.

Again, due to the high amount of water adsorption of a cellulose sponge, a large volume of water or other cleaning solution can be exposed to the cellulose sponge during rinsing. Many cellulose sponges treated with antimicrobial agents exhibit antimicrobial effectiveness, but do not have long-lasting antimicrobial activity because the antimicrobial agents wash out of the cellulose sponges upon rising with water or when the article is used in cleaning applications.

Cellulose sponges are used repeatedly prior to discarding. A consumer may use a cellulose sponge at least once a day for 30 days or more. In some instances, the cellulose sponge may be used two or more times a day for 60 days or more. During the cleaning process, often the cellulose sponge is exposed to a high volume of water. Therefore, it is important the antimicrobial efficacy within the cellulose sponge remain beyond a single use and especially beyond a series of rinses.

Incorporating biguanide within the cellulose sponge not only results in effectiveness to partially or completely kill microorganisms such as, but not limited to, bacteria, fungi, molds, mildew, and/or viruses within the cellulose sponge during packaging, but also in effectiveness to partially or completely kill microorganisms within the cellulose sponge following a series of at least 10, preferably at least 50, and more preferably at least 100 rinses of the cellulose sponge in water. A "rinse" is considered to be placing the cellulose sponge under running tap water, nearly saturating the cellulose sponge with the water, squeezing excess water from the cellulose sponge, and repeating from two to three times.

In summary, Applicant has found that although some of the biguanide is initially rinsed out of the cellulose sponge following initial use, effective amounts of biguanide are remain within the cellulose sponge to reduce microorganisms within the cellulose sponge during the intended useful life of the cellulose sponge.

One or more biguanide compounds that can be included in the cellulose sponge include, but are not limited to, compounds having the following general formula:

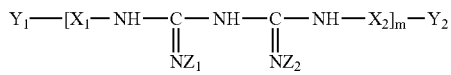

where $X_1$ and $X_2$ are hydrogen or any aliphatic, cycloaliphatic, aromatic, substituted aliphatic, substituted aromatic, heteroaliphatic, heterocyclic, or heteroaromatic compound, or a mixture of any of these. $Y_1$ and $Y_2$ are any aliphatic, cycloaliphatic, aromatic, substituted aliphatic, substituted aromatic, heteroaliphatic, heterocyclic, or heteroaromatic compound, or a mixture of any of these. M is a number equal to or greater than 1. Typically, M has an average value such that the molecular weight biguanide compound is about 1000-1400 grams/mole; however, the molecular can be higher or lower. Generally, M is about 2-20. $Z_1$ and $Z_2$ are hydrogen or a hydrogen bonded to a salt. The above-mentioned organic materials may be modified to include a thiol group in their structure so as to allow for the bonding of the compound to a metallic substrate, or may be derivatized with other functional groups to permit direct immobilization on a non-metallic substrate. The above-mentioned organic materials may also be suitably functionalized to incorporate groups such as hydroxy, amine, halogen, epoxy, alkyl or alkoxy silyl functionalities to enable direct immobilization to a surface. The salt can include salts with an inorganic acid, such as hydrochloride, hydrofluoride, nitrate, sulfate and/or phosphate, and/or salts with an organic acid, such as carboxylic acid, acetate, benzoate, tartrate, adipate, lactate, formate, maleate, glutamate, ascorbate, citrate, gluconate, oxalate, succinate, pamoate, salicylate, isethionate, succinimate, mono-diglycollate, dimethanesulfonate, di-isobutyrate, and/or glucoheptonate. Specific examples of these compounds include, but are not limited to, polyhexamethylene biguanide hydrochloride, p-chlorophenyl biguanide; and 4-chlorobenzhydryl biguanide. In another aspect of this embodiment, the biguanide compounds include, but are not limited to, halogenated hexidine such as, but not limited to, chlorhexidine (1,1'-hexamethylene-bis-5-(4-chlorophenyl biguanide) and its salts. One particularly suitable biguanide is polyhexamethylenebiguanide hydrochloride, or PHMB, marketed in the form of an aqueous solution under the name VANTOCIL IB® by Arch Chemical of Norwalk, Conn.

During processing to make the cellulose sponge, some of the cellulose is oxidized to give carboxylate groups. Biguanide is a cationic polymer. The electrostatic interaction between the positively charged cites of the biguanide and negatively charged carboxylate groups within the cellulose sponge cause the biguanide to bind. The biguanide bonds strongly within the cellulose sponge. However, due to the variability of input material and processing, the degree of binding of the biguanide within the cellulose sponges may be varied. Generally, Applicant has found that from 40 to 60% of the biguanide within the packaged cellulose sponge (unrinsed) bonds within the cellulose sponge. Due to this, Applicant has found that there is long lasting effectiveness of the biguanide to partially or completely kill microorganisms within the cellulose sponge over the intended life of the cellulose sponge.

A "used" cellulose sponge has been exposed to a series of rinses. A used cellulose sponge was determined to be one that has been exposed to a series of 100 rinses. A used cellulose sponge must maintain a minimum level of biguanide to partially or completely kill microorganisms within the cellulose sponge. Also, the biguanide compound content is typically limited by economic cost considerations, formula solubility requirements, and/or the intended use of biguanide containing product.

In one embodiment, an input solution containing from 0.05 to 1.2% wt. of biguanide is absorbed into a cellulose sponge to saturate the cellulose sponge. The cellulose sponge is squeezed of excess liquid. Generally, no rinsing occurs following absorption of the biguanide containing input solution and packaging. Prior to rinsing, a packaged cellulose sponge that contains at least 0.4% wt. biguanide, based on the dry weight of the cellulose sponge, will result in a used cellulose sponge containing at least 0.02% wt. biguanide, based on the dry weight of the cellulose sponge. For this embodiment, the used cellulose sponge maintains the ability to produce a three log reduction of microorganisms within the cellulose sponge within 24 hours of inoculation, typically within 1 hour, and more typically within 5 minutes.

In one embodiment, an input solution containing from 0.1 to 2.0% wt. of biguanide is absorbed into a cellulose sponge to saturate the cellulose sponge. The cellulose sponge is squeezed of excess liquid. Generally, no rinsing occurs following absorption of the biguanide containing input solution and packaging. Prior to rinsing, a packaged cellulose sponge that contains at least 1.25% wt. biguanide, based on the dry weight of the cellulose sponge, will result in a used cellulose sponge containing at least 0.5% wt. biguanide, based on the dry weight of the cellulose sponge. For this embodiment, the used cellulose sponge maintains the ability to produce a 100% reduction of microorganisms within the cellulose sponge within 24 hours, typically within 1 hour, and more typically within 5 minutes.

Optionally, other antimicrobial and/or antifungal agents may be incorporated into the cellulose sponge. Optional antimicrobial agents include cationic amine antimicrobial compounds, which include antimicrobial protonated tertiary amines and small molecule quaternary ammonium compounds. Quaternary ammonium compounds are generally considered "broad spectrum" antimicrobial cationic compounds having efficacy against both gram positive (e.g., *Staphylococcus* sp.) and gram negative (e.g., *Escherichia coli*) microorganisms. Thus, the quaternary ammonium compounds can be incorporated for antibacterial purposes for the cellulose sponge, while in the package, and should be present in amounts effective for such purposes. The choice of the quaternary ammonium compounds is not critical. Typically they are preferably selected from mono-long-chain, tri-short-chain, tetralkyl-ammonium compounds, di-long-chain, di-short-chain tetralkyl-ammonium compounds, and mixtures thereof. The chains may straight or branched. N-heterocyclic ring compounds are also considered quaternary ammonia compounds. Exemplary small molecule quaternary ammonium compounds include benzalkonium chloride and alkyl substituted derivatives thereof, di-long chain alkyl (C8-C18) quaternary ammonium compounds, cetylpyridinium halides and their derivatives, benzethonium chloride and its alkyl substituted derivatives, octenidine and compatible combinations thereof.

When cellulose sponges are wet they are relatively soft and flexible. However, after a cellulose sponge dries, it is hard and stiff. Therefore, cellulose sponges are typically packaged slightly moistened in a sealed plastic wrap. Due to the moisture in the package, microorganism growth can occur while the cellulose sponge is in the package, prior to initial use. Various methods exist to preserve products and promote package stability, including the use of antimicrobial agents, preservatives, and sterilization techniques. Water activity ($a_w$) is a measurement of the energy status of the water in a system. Water activity is sometimes defined as "free", "bound", or "available water" in a system. Controlling water activity of the cellulose sponge in the package will control the amount of water available to promote microorganism growth while in the package. Many microorganisms, such as bacteria, prefer a water activity level of 0.99 and most need higher than 0.91 to grow. Adding humectants like salts and sugar 'bind' the water to lower the water activity and therefore control microorganism growth. Therefore, for preservation of the cleaning product while in the package, humectants can be included to provide a water activity of less than 0.91.

Aside from the possible antimicrobial impact, including a humectant creates a soft and flexible cellulose sponge within the package and for use immediately after opening the package. However, the humectant does not remain in the cellulose sponge once the cellulose sponge has been rinsed.

In the Examples below, Applicant has found that that from 40 to 60% of the biguanide within the packaged sponge is retained within the cellulose sponge following rinsing, and the retention does not appear to be dependent on the concentration of the humectant. For a cellulose sponge, which a user intends to use repeatedly over time, retention of the antimicrobial agent within the cellulose sponge is desirable. Applicant's learning's show that concentration of humectant does not impact retention of the biguanide within the cellulose sponge and the amount of humectant should be chosen based on other factors such as the desired water activity or the desired "softness" the humectant gives the packaged cellulose sponge.

There are a variety of ways to introduce the humectant into the cellulose sponge. One way may be to include the humectant in the input solution absorbed into the cellulose sponge prior to packaging. The biguanide may be included in the humectant solution or the biguanide may be absorbed into the cellulose sponge before or after the humectant is introduced into the cellulose sponge.

Suitable humectants may include a cationic salt. Salts are desirable humectant in that such compounds are generally inexpensive when compared to many types of cationic antimicrobial agents. A variety of different salts can be used such as, but not limited to, monovalent salts, divalent salts, organic salts, and the like. These salts include, but are not limited to, acetates, acetylides, ammonium salts (excluding quats), arsenates, astatides, azides, bihalide salts, bicarbonates, bisulfides, borides, borohydrides, borohalides, carconates, citrates, cyanates, cyanides, formates, germanates, glycinates, halates, halides, hydrides, hydroselenides, hydrosulphides, hydroxides, imides, metaniobates, metaantalates, metavanadates, nitrates, nitrides, nitrites, oxides, perchlorates, phosphates, phosphonium salts, selenides, selenites, selenates, sulphides, sulphates, ternary salts, tetraalkyl-ammonium salts, tellurides, thiocyanates, and/or vanadates. In one aspect of this embodiment, the antimicrobial agent includes, but is not limited to, potassium citrate, sodium citrate, sodium tartrate, potassium tartrate, potassium lactate, sodium lactate, salicylate salts of sodium and/or potassium, magnesium sulphate, magnesium chloride, sodium chloride, ammonium chloride, and/or potassium chloride.

In one embodiment, the humectant is $MgCl_2$. If including the $MgCl_2$ for achieving a water activity of less than 0.91, then at least 10% wt. of the input solution should be $MgCl_2$. However, too high of a humectant can cause precipitation. Therefore, the $MgCl_2$, if included, should not be more than 14% wt. of the input solution.

To make an antimicrobial cellulose sponge as described in this disclosure, a rinsed regenerated cellulose sponge is exposed to an input solution containing biguanide. The rinsed regenerated cellulose sponge generally has a moisture content from 40 to 70% water. Alternatively, the biguanide containing input solution may be absorbed into a dry cellulose sponge. The input solution is absorbed by the cellulose sponge and saturates the cellulose sponge. Generally, the input solution contains from 0.05 to 2.0% wt. biguanide to result in a used cellulose sponge maintaining a sufficient level of biguanide to partially or completely kill microorganisms within the cellulose sponge. The input solution may additionally include a humectant or another antimicrobial agent. Alternatively, the humectant or other antimicrobial agent, if included, may be introduced and absorbed into the cellulose sponge prior to the absorption of the biguanide or following the absorption of the biguanide.

Following absorption of the input solution into the cellulose sponge, the cellulose sponge is squeezed of excess liquid. Then, the cellulose sponge may be converted to the appropriate size and packaged in a sealed film. In one embodiment, the packaged cellulose sponge typically contains at least 0.4% wt. biguanide, based on the dry weight of the cellulose sponge, to achieve a used cellulose sponge that maintains at least 0.02% wt. biguanide, based on the dry weight of the cellulose sponge, which is a sufficient amount to partially or completely kill microorganisms within the cellulose sponge. In another embodiment, the packaged cellulose sponge typically contains at least 1.25% wt. biguanide, based on the dry weight of the cellulose sponge, to achieve a used cellulose sponge that maintains at least 0.5% biguanide, based on the dry weight of the cellulose sponge, which is a sufficient amount to partially or completely kill microorganisms within the cellulose sponge.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

EXAMPLES

Preparation of Antimicrobial Solution

A commercially available biguanide solution (Vantocil IB, Polyhaxamethylene Biguanide hydrochloride, available from Arch Chemical Company of Cheshire, Conn.) 20% by weight was diluted with water to obtain a desired biguanide concentration.

Preparation of Cellulose Sponge

Cellulose sponge blocks were manufactured by the conventional process (viscose process with electrical coagulation). The cellulose sponge blocks are then rinsed through hot water, bleached with a water solution containing hypochlorite, rinsed with water, and rinsed with magnesium chloride ($MgCl_2$) before converting and packaged. Alternatively, a packaged cellulose sponge, such as O-Cel-O® sponge or a Scotch-Brite® scrub sponge, both available from 3M Company of St. Paul, Minn. was used.

For any of the above cellulose sponges, the cellulose sponge was rinsed to remove any magnesium chloride by placing the cellulose sponge under running tap water, nearly saturating the cellulose sponge with the water, squeezing by hand excess water from the cellulose sponge, and repeating 50 times to arrive at a prepared cellulose sponge.

Biguanide into Cellulose Sponge

The biguanide compound in the form of solution with or without $MgCl_2$ was absorbed into the prepared cellulose sponge to saturate the cellulose sponge and form an antimicrobial cellulose sponge. Excess liquid was squeezed from the cellulose sponge. The biguanide was extracted from the cellulose sponge, and the extracted solution was tested for biguanide by absorption spectrophotometry (Beckman DU 640 Spectrophotometer purchased through Beckman Instruments Inc. of Fullerton, Calif.).

Test Methods and Materials

Articles made in the Examples below were evaluated according to the following methodology.

Water Rinsing Protocol

The water rinsing protocol to simulate a sponge that has been used consisted of saturating the biguanide containing cellulose sponge with water and thereafter wringing by hand the saturated cellulose sponges. Generally, the water was running tap water. The rinsing and wringing cycle was repeated and the number of times the cycle was repeated is indicated in the data. Generally, the rinsing and wringing cycle was repeated 50 or 100 times.

Bacterial Kill Assay (Reference AATCC 100)

The "kill assay" or preservative test determines the efficacy of an antimicrobial agent during a predetermined time course. The pass/fail indicator for this test is usually a three logarithm reduction in the numbers of microorganisms introduced into the object to be tested.

The prepared cellulose sponges were absorbed with the biguanide containing input solution, and then subjected to a water rinsing protocol to allow an evaluation of durability of antimicrobial treatment for the cellulose sponges. In this test, the water rinsing protocol involved submerging the cellulose sponge in DI water, instead of under running tap water. The samples were then placed in a plastic bag.

A suspension of the bacteria to be used in the testing was made in a 0.1% peptone water solution of the same turbidity as a 0.5 McFarland Equivalence Turbidity Standard. This standard typically yields a bacterial count of approximately $1.5 \times 10^8$ colony forming units (CFU) per milliliter. Cellulose sponge samples were cut into 1.5"×2.5"×1.0" inch sizes (face area 3.75 $in^2$). The cellulose sponges were supplied as duplicates. Test Organism used were as followed:
 a. *Salmonella choleraesuis* subsp. *Choleraesuis* serovar *typhimurium* (ATCC 14028; now called *Salmonella enterica* subsp. *enterica* in the ATCC bank)
 b. *Pseudomonas aeruginosa* (ATCC 15442) or *Pseudomonas putida*
 c. *Staphylococcus aureus* (ATCC 6538)
 d. *Escherichia Coli* (ATCC11229)
 e. *Shewanella putrefaciens* (ATCC 8071)

The test cellulose sponges were placed into sterile Whirlpak™ bags. A 100 μl inoculum was added to 22 ml of peptone water and used to inoculate the cellulose sponge. To mix the bacteria, the cellulose sponge was squeezed repeatedly manually inside the bag in order to uniformly distribute the bacterial suspension and allow the liquid to reabsorb into the cellulose sponge. The bags with cellulose sponges were allowed to incubate at room temperature (20-25° C.) throughout the experiment. For the zero and 24 hours reading, the cellulose sponge bacterial population was measured after 5 minutes and 24 hours of contact time, respectively.

The sampling of the cellulose sponges occurred at time points after inoculation: 5 minutes (immediately after inoculation) and 24 hours. The liquid was squeezed from the cellulose sponge and 100 μl of solution was withdrawn from the bag. The extract was placed into 9.9 mL of Peptone water and mixed by vortexing. Serial dilutions were plated on 3M Petrifilm™ plate (1 mL) until a countable range was achieved. Plates were incubated at 35° C. for 24 hours and counted using a 3M Petrifilm™ plate reader.

Fungal Challenge Test (Reference ASTM G21-96)

The prepared cellulose sponges were absorbed with the biguanide containing input solution, and then subjected to a water rinsing protocol to allow an evaluation of durability of antimicrobial treatment for the cellulose sponges. In this test, the water rinsing protocol involved submerging the cellulose sponge in DI water, instead of under running tap water. The samples were then placed in a plastic bag.

The cellulose sponges were tested with standardized test method ASTM G21-96 by aerosolizing a mixed fungal spore suspension of known concentration onto the sample surface and incubating the material at 28° C./95% relative humidity for 28 days. The test cellulose sponges were aseptically placed onto the surface of a minimal salts (M-9) agar plate and inoculated. The media used did not contain a carbon source. Therefore, fungal growth indicated breakdown of the sample components. The standard test used the following organisms:

| Fungi | ATCC No. |
|---|---|
| Aspergillus niger | 9642 |
| Penicillium pinophilumC | 11797 |
| Chaetomium globosum | 6205 |
| Gliocladium virens | 9645 |
| Aureobasidium pullulans | 15233 |

The sampling of the cellulose sponges occurred at time points after inoculation: day 5, day 12, day 15, and day 29. The test cellulose sponges were examined for the presence of fungal growth, and the level of growth was rated as shown below. A piece of sterile filter paper was also inoculated to serve as a positive control.

| Rating Scale: | 0 | No growth |
|---|---|---|
| | 1 | 0-10% coverage, trace growth |
| | 2 | 10-30% coverage, light growth |
| | 3 | 30-60% coverage, moderate growth |
| | 4 | >60% coverage, heavy growth |

Water Activity ($a_w$) in the Cellulose Sponges

Water activity ($a_w$) is a measure of the amount of free water available to a microorganism to support growth. Water activity expresses the active portion of the water content as opposed to the total moisture content, which includes "bound water." The measurements were conducted using the AquaLab CX-2 by Decagon Devices, Inc. by utilizing the chilled mirror/dew point hygrometric methodology for determining water activity. The cellulose sponge was cut into a disk having a 1.5" inch diameter and 1/16 inch thick.

EXAMPLES

The following examples further illustrate aspects of the invention. Unless otherwise indicated, all parts and percentages are by weight.

Example 1

The liquid biguanide solution from Table 1 was introduced to prepared cellulose sponges and cellulose sponges laminated to a scouring web by absorption of the liquid biguanide solution into the cellulose sponge to saturate the cellulose sponge. The excess solution was squeezed from the cellulose sponge and the cellulose sponge was placed in a package. Then the cellulose sponge was subject to the water rinsing protocol to simulate a used cellulose sponge, with the number of rinsing/wringing cycles indicated.

TABLE 1

| Biguanide solution | | | | | | |
|---|---|---|---|---|---|---|
| | Input Solution Formulations (wt. %) | | | | | |
| | 1 | 2 | 3 | 4 | 5 | 6 |
| Biguanide | 0.0% | 0.05% | 0.10% | 0.20% | 0.20% | 0.50% |
| $MgCl_2$ | 10% | 0% | 0% | 0% | 10% | 0% |
| Water | 90% | 99.95% | 99.9% | 99.8% | 89.8% | 99.5% |

The cellulose sponges were tested according to the Bacterial Kill Assay and the Fungal Challenge Test. The data is presented in Table 2 to Table 4.

TABLE 2

| Bacterial Kill Assay (AATCC 100) | | | | | |
|---|---|---|---|---|---|
| | | wt. % Biguanide (based on dry sponge) | | Plate Counts (cfu) for a Used Cellulose sponge | |
| Samples | Formulation | Package | Used** | 5 mins | 24 hrs |
| | | *Escherichia Coli* | | | |
| Untreated Sponge | 1 | 0 | 0 | 8.28E+07 | 1.63E+08 |
| Treated Sponge | 6 | 3 | 0.7 | <1 | <1 |
| Treated Sponge | 4 | 2 | 0.6 | <1 | <1 |
| Treated Sponge | 3 | 1.6 | 0.4 | 2.00E+02* | <1 |
| Treated Sponge | 2 | 1 | 0.05 | 5.90E+03* | <1 |

TABLE 2-continued

Bacterial Kill Assay (AATCC 100)

| Samples | Formulation | wt. % Biguanide (based on dry sponge) | | Plate Counts (cfu) for a Used Cellulose sponge | |
|---|---|---|---|---|---|
| | | Package | Used** | 5 mins | 24 hrs |
| *Shewanella putrefaciens* | | | | | |
| Untreated Sponge | 1 | 0 | 0 | 4.44E+05 | 1.01E+06 |
| Treated Sponge | 6 | 3 | 0.7 | <1 | <1 |
| *Staphylococcus aureus* | | | | | |
| Untreated Sponge | 1 | 0 | 0 | 4.44E+05 | 1.01E+06 |
| Treated Sponge | 6 | 3 | 0.7 | <1 | <1 |
| *Pseudomonas aeruginosa* | | | | | |
| Untreated Sponge | 1 | 0 | 0 | 1.87E+06 | 2.80E+06 |
| Treated Sponge | 6 | 3 | 0.7 | <1 | <1 |

*Plates did not have any growth on the first dilution possibly due to antimicrobial agent activities.
**Used = 100 rinsing/wringing cycles

TABLE 3

Fungal Challenge (ASTM G21-96) for Cellulose Sponge

| Formulation 6 | Rinse Cycles | wt. % Biguanide (based on dry sponge) | Day 7 | Day 14 | Day 21 | Day 28 |
|---|---|---|---|---|---|---|
| Untreated Sponge | 50x | 0 | 1, 1, 1 | 3, 3, 3 | 4, 4, 4 | 4, 4, 4 |
| Treated Sponge | 0x | 3 | 0, 0, 0 | 0, 0, 0 | 0, 0, 0 | 0, 0, 0 |
| Treated Sponge | 50x | 0.7 | 0, 0, 0 | 0, 0, 0 | 0, 0, 0 | 0, 0, 0 |
| Treated Sponge | 100x | 0.7 | 0, 0, 0 | 0, 0, 0 | 0, 0, 0 | 0, 0, 0 |

TABLE 4

Fungal Challenge (ASTM G21-96) for Cellulose Sponge with a Scouring Web

| Formulation 5 | Rinse Cycles | wt. % Biguanide (based on dry sponge) | Day 7 | Day 14 | Day 21 | Day 28 |
|---|---|---|---|---|---|---|
| Untreated - Sponge side | 50x | 0 | 4, 4 | 4, 4 | 4, 4 | 4, 4 |
| Treated Sponge - Sponge side | 0x | 0.8 | 0 | 0 | 0 | 0 |
| Treated Sponge - Sponge side | 10x | 0.3 | 0 | 0 | 0 | 0 |
| Treated Sponge - Sponge side | 50x | 0.2 | 0 | 0 | 0 | 0 |
| Treated Sponge - Sponge side | 100x | 0.2 | 0 | 0 | 0 | 0 |

Example 2

Antimicrobial cellulose sponges were prepared by soaking a prepared cellulose sponge in a solution containing one of the formulations given in Table 5 below for 20 minutes. The antimicrobial cellulose sponges were also prepared by soaking a prepared cellulose sponge in the input biguanide solution for 20 minutes and then soaking in the MgCl$_2$ solution for less than 5 minutes. After soaking, the cellulose sponges were squeezed out between squeeze rolls, and then immediately placed into plastic bags for packaging.

The rinsing protocol consisted of saturating the cellulose sponges in a large amount of DI water and thereafter wringing the saturated cellulose sponges, with the rinsing/wringing cycle being repeated as many as 10 times per sample. The samples were then placed in a plastic bag.

TABLE 5

Biguanide Solution with Humectants

| Component | Formulation |
|---|---|
| Biguanide | 0.05%-2% |
| MgCl2 | 1%-14% |
| NaCl | 1%-16% |
| Water | Add to 100% |

The data presented in Table 6 show that humectant concentration does not seem to greatly impact the retention of the biguanide in the cellulose sponges after rinsing. Retention involves a comparison between the biguanide within the packaged cellulose sponge (no rinses) and the biguanide within the cellulose sponge following 10 cycles of the rinsing and wringing cycle.

TABLE 6

Biguanide Retention in Cellulose Sponges

| Experimental Conditions | wt. % Biguanide (based on dry sponge) | | % Biguanide Retention |
|---|---|---|---|
| | Before Rinsing (packaged) | After Rinsing (10 rinses) | |
| One step addition | | | |
| 0% MgCl$_2$, 0.2% Biguanide | 2.24 | 1.10 | 49 |
| 1% MgCl$_2$, 0.2% Biguanide | 0.62 | 0.41 | 66 |
| 1% MgCl$_2$, 0.5% Biguanide | 1.30 | 0.70 | 54 |
| 5% MgCl$_2$, 0.2% Biguanide | 0.64 | 0.39 | 60 |
| 5% MgCl$_2$, 0.5% Biguanide | 1.54 | 0.65 | 42 |
| 3% MgCl$_2$, 0.35% Biguanide | 0.99 | 0.61 | 62 |
| 8% MgCl$_2$, 0.5% Biguanide | 1.15 | 0.75 | 55 |
| | 1.36 | 0.61 | |
| 10% MgCl$_2$, 0.5% Biguanide | 1.26 | 0.58 | 46 |
| 12% MgCl$_2$, 0.5% Biguanide | 0.79 | 0.40 | 49 |
| | 0.89 | 0.42 | |
| 12% MgCl$_2$, 1.0% Biguanide | 1.18 | 0.53 | 45 |
| 14% MgCl$_2$, 1.0% Biguanide | 0.27 | 0.13 | 50 |
| 1% NaCl, 0.3% Biguanide | 0.50 | 0.24 | 48 |
| 12% NaCl, 0.3% Biguanide | 1.46 | 0.81 | 55 |
| 16% NaCl, 0.6% Biguanide | 0.27 | 0.16 | 59 |
| Two steps addition (Biguanide followed by MgCl$_2$) | | | |
| 10% MgCl$_2$, 0.43% Biguanide | 0.50 | 0.20 | 40 |
| 10% MgCl$_2$, 0.8% Biguanide | 1.06 | 0.59 | 55 |
| 10% MgCl$_2$, 1.1% Biguanide | 0.91 | 0.43 | 47 |

Example 3

A commercially available magnesium chloride hexahydrate (MgCl$_2$.6H$_2$O) (EMD Chemical Company, Gibbstown, N.J.), sodium chloride (NaCl) (Fisher Scientific Company, Fair Lawn, N.J.), potassium chloride (KCl) (EMD Chemical Company, Gibbstown, N.J.), and glycerol (EMD Chemical Company, Gibbstown, N.J.) was mixed to obtain a desired concentration. The solution was measured for water activity using the AquaLab CX-2 by Decagon Devices, Inc. The water activity for those solutions is presented in Table 7.

TABLE 7

Water Activity of Various Humectant Solutions

| Solution Concentration | MgCl$_2$ | NaCl | KCl | Glycerol | K$_2$CO$_3$ |
|---|---|---|---|---|---|
| 0% | 0.992 | 0.992 | 0.992 | 0.992 | 0.992 |
| 8% | 0.944 | 0.949 | 0.952 | 0.975 | 0.973 |
| 10% | 0.926 | 0.936 | 0.950 | 0.971 | 0.960 |
| 12% | 0.904 | 0.919 | 0.938 | 0.966 | 0.957 |
| 14% | 0.876 | — | 0.928 | 0.962 | — |
| 16% | 0.847 | 0.887 | 0.915 | 0.955 | 0.943 |
| 18% | 0.841 | — | 0.904 | 0.950 | — |
| 20% | 0.768 | 0.842 | 0.891 | 0.944 | 0.925 |
| 22% | — | — | 0.875 | 0.939 | — |
| 24% | — | — | 0.859 | 0.934 | — |
| 50% | — | — | — | 0.811 | — |

Example 4

A prepared cellulose sponge was soaked for 20 minutes in one of the MgCl$_2$ or NaCl humectant solutions from Example 3. After soaking, the cellulose sponge was squeezed out between squeeze rolls and then immediately placed into airtight plastic bags. The samples were tested for water activity within 24 hours.

Magnesium chloride and sodium chloride reduce water activity levels of the cellulose sponge. The data presented in Table 8 shows the water activity of cellulose sponges can be reduced below 0.91 with sufficient concentrations of MgCl$_2$ and NaCl in water.

TABLE 8

Water Activity of Various Humectants in Cellulose Sponges

| Concentration (wt. % of Input Solution) | MgCl2 | NaCl |
|---|---|---|
| 0% | 0.992 | 0.992 |
| 10% | 0.913 | 0.926 |
| 12% | 0.896 | 0.921 |
| 14% | 0.890 | 0.900 |
| 16% | — | 0.881 |

What is claimed is:

1. A method of maintaining the ability of a cleaning structure to be antimicrobial, the method consisting of:
providing an anionically functionalized cellulose sponge, wherein the anionic functional groups are formed during the manufacture of the cellulose sponge;
absorbing into the cellulose sponge an input solution consisting of water and biguanide having cationic functional groups;
bonding the cationic functional groups of the biguanide to the anionic functional groups of the cellulose sponge; and
packaging the cellulose sponge with biguanide bonded thereto in a sealed package;
wherein the packaged cellulose sponge optionally includes a material selected from the group consisting of a dye, a perfume, a fragrance, a surfactant, and reinforcing fibers;
wherein the packaged cellulose sponge does not include humectant; and
wherein the cellulose sponge maintains at least 0.02 weight percent bonded biguanide, based on a dry weight of the cellulose sponge, following 100 cycles of rinsing and wringing with water to provide at least a three log reduction in microorganisms in the cellulose sponge.

2. The method of claim 1, wherein the reduction in microorganism in the cellulose sponge occurs within 5 minutes.

3. The method of claim 1, wherein the cellulose sponge maintains at least 0.5 weight percent bonded biguanide, based on the dry weight of the cellulose sponge, following 100 cycles of rinsing and wringing with water, to provide a 100% reduction of microorganisms in the cellulose sponge.

4. The method of claim 1, wherein the packaged cellulose sponge contains at least 0.4 weight percent bonded biguanide, based on the dry weight of the cellulose sponge.

5. The method of claim 4, wherein the packaged cellulose sponge contains at least 1.25 weight percent bonded biguanide, based on the dry weight of the cellulose sponge.

6. The method of claim 4, wherein the cellulose sponge maintains at least 0.5 weight percent bonded biguanide, based on the dry weight of the cellulose sponge, following 100 cycles of rinsing and wringing with water, to provide a 100% reduction of microorganisms in the cellulose sponge within 5 minutes.

7. The method of claim 1, wherein the biguanide has the formula:

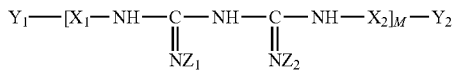

wherein:
X$_1$ and X$_2$ are hydrogen or an aliphatic, cycloaliphatic, aromatic, substituted aliphatic, substituted aromatic, heteroaliphatic, heterocyclic, or heteroaromatic compound, or a mixture of any of these;
Y$_1$ and Y$_2$ are an aliphatic, cycloaliphatic, aromatic, substituted aliphatic, substituted aromatic, heteroaliphatic, heterocyclic, or heteroaromatic compound, or a mixture of any of these;
M is a number equal to or greater than 1; and
Z$_1$ and Z$_2$ are hydrogen.

8. A method of making an antimicrobial cleaning article, the method consisting of:
providing an anionically functionalized cellulose sponge, wherein the anionic functional groups are formed during the manufacture of the cellulose sponge;
absorbing into the cellulose sponge an input solution consisting essentially of water and biguanide having cationic functional groups;
bonding the cationic functional groups of the biguanide to the anionic functional groups of the cellulose sponge; and
packaging the cellulose sponge with biguanide bonded thereto in a sealed package;
wherein the packaged cellulose sponge optionally includes a material selected from the group consisting of a dye, a perfume, a fragrance, a surfactant, and reinforcing fibers; and
wherein the packaged cellulose sponge does not include humectant.

9. The method of claim 8, wherein the biguanide has the formula:

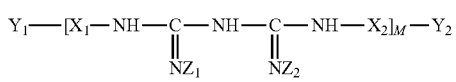

wherein:
X$_1$ and X$_2$ are hydrogen or an aliphatic, cycloaliphatic, aromatic, substituted aliphatic, substituted aromatic, heteroaliphatic, heterocyclic, or heteroaromatic compound, or a mixture of any of these;
Y$_1$ and Y$_2$ are an aliphatic, cycloaliphatic, aromatic, substituted aliphatic, substituted aromatic, heteroaliphatic, heterocyclic, or heteroaromatic compound, or a mixture of any of these;
M is a number equal to or greater than 1; and
Z$_1$ and Z$_2$ are hydrogen.

10. A packaged antimicrobial cleaning article made by the method of claim 8.

11. A packaged antimicrobial cleaning article made by the method of claim 9.

12. An antimicrobial sponge consisting essentially of a cellulose sponge, water, and biguanide bonded to the cellulose sponge through the interaction of cationic functional groups on the biguanide and anionic functional groups on the cellulose sponge; wherein the cellulose sponge maintains at least 0.02 weight percent bonded biguanide, based on a dry weight of the cellulose sponge, following 100 cycles of rinsing and wringing with water to provide at least a three log reduction in microorganisms in the cellulose sponge; wherein the cellulose sponge optionally includes a material selected from the group consisting of a dye, a perfume, a fragrance, a surfactant, and reinforcing fibers; and wherein the cellulose sponge does not include humectant.

13. The antimicrobial sponge of claim 12, wherein the biguanide has the formula:

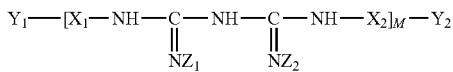

wherein:
X$_1$ and X$_2$ are hydrogen or an aliphatic, cycloaliphatic, aromatic, substituted aliphatic, substituted aromatic, heteroaliphatic, heterocyclic, or heteroaromatic compound, or a mixture of any of these;
Y$_1$ and Y$_2$ are an aliphatic, cycloaliphatic, aromatic, substituted aliphatic, substituted aromatic, heteroaliphatic, heterocyclic, or heteroaromatic compound, or a mixture of any of these;
M is a number equal to or greater than 1; and
Z$_1$ and Z$_2$ are hydrogen.

* * * * *